(12) United States Patent
Deladurantaye et al.

(10) Patent No.: US 10,390,883 B2
(45) Date of Patent: Aug. 27, 2019

(54) LASER-DIRECTED MICROCAVITATION

(71) Applicant: INSTITUT NATIONAL D'OPTIQUE, Quebec (CA)

(72) Inventors: Pascal Deladurantaye, Quebec (CA); Ozzy Mermut, Quebec (CA)

(73) Assignee: INSTITUT NATIONAL D'OPTIQUE, Quebec (CA)

( * ) Notice: Subject to any disclaimer, the term of this patent is extended or adjusted under 35 U.S.C. 154(b) by 0 days.

(21) Appl. No.: 15/670,277

(22) Filed: Aug. 7, 2017

(65) Prior Publication Data
US 2018/0021086 A1 Jan. 25, 2018

Related U.S. Application Data

(63) Continuation of application No. 14/724,440, filed on May 28, 2015, now abandoned.
(Continued)

(51) Int. Cl.
*A61B 18/20* (2006.01)
*A61B 18/22* (2006.01)
(Continued)

(52) U.S. Cl.
CPC .............. *A61B 18/20* (2013.01); *A61B 18/22* (2013.01); *A61F 9/008* (2013.01);
(Continued)

(58) Field of Classification Search
CPC ..... A61F 9/008; A61F 9/00814; C12N 13/00; G01N 33/50; A61B 18/20; A61B 18/22;
(Continued)

(56) References Cited

U.S. PATENT DOCUMENTS 7,974,319 B2    7/2011  Deladurantaye et al.
8,073,027 B2 *  12/2011 Deladurantaye ...... G06F 1/0321
                                                        372/25
(Continued)

OTHER PUBLICATIONS

Roider et al., Selective retinal pigment epithelium laser treatment, Theoretical and clinical aspects, Lasers in Ophthalmology—Basic, Diagnostic and Surgical Aspects, p. 119-129, 2003.
(Continued)

*Primary Examiner* — Michael W Kahelin
*Assistant Examiner* — Vynn V Huh
(74) *Attorney, Agent, or Firm* — Erise IP, P.A.

(57) ABSTRACT

Methods and systems for the controlled generation of bubbles in a medium having a liquid phase are generally provided. Laser pulses having a time-dependent pulse parameter controllable over their duration are generated. The medium is irradiated with the laser pulses with a radiant exposure sufficient to initiate microcavitation within the medium during each laser pulse. The time-dependent pulse parameter of each laser pulse is controlled according to a generally positive variation over the pulse duration such that the medium absorbs a greater quantity of energy from the laser pulse at an end of the pulse duration than at a beginning thereof. Such methods and systems may be used for various applications such as biology, medicine or material processing.

9 Claims, 9 Drawing Sheets

Related U.S. Application Data

(60) Provisional application No. 62/003,740, filed on May 28, 2014.

(51) Int. Cl.
| | | |
|---|---|---|
| *A61F 9/008* | (2006.01) | |
| *A61B 17/00* | (2006.01) | |
| *A61B 18/00* | (2006.01) | |
| *C12N 13/00* | (2006.01) | |
| *G01N 33/50* | (2006.01) | |

(52) U.S. Cl.
CPC .......... *A61F 9/00814* (2013.01); *C12N 13/00* (2013.01); *G01N 33/5005* (2013.01); *A61B 2017/00159* (2013.01); *A61B 2017/00185* (2013.01); *A61B 2018/00511* (2013.01); *A61B 2018/00535* (2013.01); *A61B 2018/00577* (2013.01); *A61B 2018/206* (2013.01); *A61B 2018/2035* (2013.01); *A61B 2018/20355* (2017.05); *A61B 2018/2255* (2013.01)

(58) Field of Classification Search
CPC ........... A61B 2017/00159; A61B 2017/00185; A61B 2018/00511; A61B 2018/00535; A61B 2018/00577; A61B 2018/2035; A61B 2018/206
USPC .......................................................... 606/2.5
See application file for complete search history.

(56) References Cited

U.S. PATENT DOCUMENTS

| | | | |
|---|---|---|---|
| 8,254,015 B2 | 8/2012 | Taillon et al. | |
| 2004/0039378 A1* | 2/2004 | Lin | A61B 18/20 606/6 |
| 2006/0111697 A1* | 5/2006 | Brinkmann | A61B 18/20 606/4 |
| 2011/0077528 A1 | 3/2011 | Kemp et al. | |

OTHER PUBLICATIONS

Neumann et al., Self-limited growth of laser-induced vapor bubbles around single microabsorbers, Applied Physics Letters 93, 033901, 2008.

Brinkmann et al., Selective RPE-Photodestruction: Mechanism of cell damage by pulsed laser irradiance in the ns to us time regime, Part of the SPIE Conference on Laser-Tissue Interaction X: Photochemical, Photothermal and Photomechanical, SPIE vol. 3601, p. 59-65, Jan. 1999.

Framme et al., Investigation of Selective Retina Treatment (SRT) by means of 8 ns laser pulses in a rabbit model, Lasers in Surgery and Medecine 40, p. 20-27, 2008.

In Taek Kim et al., Melanosomes of retinal pigment epithelium—Distribution, shape and acid phosphatase activity, Korean J. Ophthalmol., vol. 12, p. 85-91, 1998.

Lukianova-Hleb et al., Hemozoin-generated vapor nanobubbles for transdermal reagent—and needle-free detection of malaria, PNAS Early Edition, p. 1-6, 2013.

Lukianova-Hleb et al., Supporting Information, www.pnas.org/cgi/content/short/1316253111, 2013.

Neumann et al., Microbubble dynamics around laser heated microparticles, Therapeutic Laser Applications and Laser-Tissue Interactions, Proceedings of SPIE-OSA Biomedical Optics, SPIE vol. 5142, p. 82-87, 2003.

Brinkmann et al., Selective Retina Therapy (SRT): A review on methods, techniques, preclinical and first clinical results, Bull. Soc. belge Ophtalmol., 302, p. 51-69, 2006.

Deladurantaye et al., Ultra Stable, Industrial Green Tailored Pulse Fiber Laser with Diffraction-limited beam Quality for Advanced Micromachining, J. Phys: Conf. Ser. 276 012017, p. 1-9, 2011.

Declaration of Pascal Deladurantaye and Suzie Dufour Under 37 C.F.R. § 1.132 dated Jan. 31, 2019; U.S. Appl. No. 15/670,277, filed Aug. 7, 2017.

Roider, Johann et al.; "Selective retinal pigment epithelium laser treatment, Theoretical and clinical aspects;" Lasers in Ophthalmology—Basic, Diagnostic and Surgical Aspects; 2003; pp. 119-129; Kugler Publications, The Hague, The Netherlands.

* cited by examiner

LASER-DIRECTED MICROCAVITATION

This application is a Continuation of U.S. patent application Ser. No. 14/724,440, filed 28 May 2015, which claims benefit of U.S. Patent Application Ser. No. 62/003,740, filed 28 May 2014 and which applications are incorporated herein by reference. To the extent appropriate, a claim of priority is made to each of the above disclosed applications.

TECHNICAL FIELD

The present invention relates to microcavitation techniques and more particularly concerns the use of laser pulse shaping to control the generation of microbubbles in a medium having a liquid phase.

BACKGROUND

Laser-directed microcavitation is a photomechanical interaction involving the generation of vapor bubbles within a medium possessing a liquid phase, upon absorption of pulsed laser energy by the medium. The medium can be homogeneous comprising only the liquid phase, or can be heterogeneous and comprises the liquid phase mixed with one or more solid phases. For laser pulse durations shorter than a few microseconds, microcavitation can be a dominant mechanism causing alterations of the medium in which it is taking place. As laser energy is absorbed by the medium, the medium temperature rises at a rate that depends on the characteristics of both the medium and the laser beam. Above a certain threshold temperature, vaporization of the medium occurs and one or several vapor bubbles starts to expand. During bubble expansion, the vapor cools down and the bubble's internal pressure decreases. At some moment during the process, the bubble's internal pressure is no longer sufficient to overcome the external pressure, and a maximum bubble volume is reached as the expansion stops. A contraction phase follows, after which the bubble disappears. Following the first expansion-collapse cycle, additional oscillations with decreasing maximum bubble volumes can be observed.

In general, the total volume of medium potentially altered by laser-directed microcavitation is determined by two principal contributions. A first contribution involves thermally-induced effects, for which the affected volume is determined by the diffusion of heat within the medium as a result of the absorption of laser energy. A second contribution includes mechanically-induced alterations originating from stresses developing in the medium as the microcavitation bubbles expand and collapse. In the latter case, the mechanically-affected volume of medium around the bubble's center is at least as large as the maximum volume of the cavitation bubble.

An example of a heterogeneous medium is the cytoplasm of cells, particularly pigmented cells where the pigments absorb the energy. Selective Retina Therapy (SRT) is an example of an application which may involve or exploit laser-directed microcavitation. The absorption of laser light by melanin pigments synthetized in the melanosomes, which are membrane-bound organelles of the Retinal Pigment Epithelium (RPE) cells, can be exploited to selectively alter these cells. For such applications, it is often critical and difficult to predict and control the total volume of medium affected thermally and photomechanically. Currently, documented work examining the influence of time-domain irradiation parameters on the spatial extent of thermal and photomechanical alterations produced by microcavitation has mainly focused on the impact of the laser pulse duration. For example, it is well-known that as the pulse duration is reduced, the threshold radiant exposure to initiate microcavitation is also reduced because of improved thermal confinement (R. Brinkmann et al., "*Selective RPE photodestruction: mechanism of cell damage by pulsed-laser irradiance in the ns to µs time regime*", Proc. SPIE 3601, Laser-Tissue Interaction X: Photochemical, Photothermal, and Photomechanical, (Jun. 14, 1999)). As the pulse duration becomes short compared to the characteristic heat diffusion time within the medium, steeper temperature gradients can be locally produced because heat has less time to diffuse away during exposure to the pulse. The critical temperature for bubble formation can thus be reached with less energy delivered to the medium, because less energy escapes from the absorption centers present in the medium during exposure to the pulse. Short pulses are therefore more attractive than long pulses from a purely thermal point of view, because microcavitation can be triggered with lower energy levels of laser energy and with better spatial confinement of the thermally-induced alterations.

On the other hand, it is also well-known that as the pulse duration is shortened, the vaporization tends to become more explosive (J. Neumann and R. Brinkmann, "*Microbubble dynamics around laser heated microparticles*", in Therapeutic Laser Applications and Laser-Tissue Interactions, R. Steiner, ed., Proc. SPIE 5142, paper 5142_82 (Oct. 17, 2003)). With shorter pulses, the maximum bubble volume increases more rapidly with radiant exposure, making the control of the bubble volume more challenging. Therefore, the benefit of using shorter pulses from a thermal perspective can be cancelled by the risk of losing control over the volume of medium altered photomechanically. As a consequence, trade-offs involving longer pulse durations have been so far necessary to mitigate this risk, which lead to sacrifices on the thermal confinement.

A closer look at the distribution of melanosomes inside RPE cells is instructive for understanding the importance of controlling cavitation bubbles and heat diffusion in SRT procedures. As illustrated in FIG. 1 (PRIOR ART), melanosomes tend to gather on the apical side of RPE, close to the RPE-photoreceptor interface, and the distance between individual melanosomes and the photoreceptors can be as small as 1 µm or even in the sub-micron range. As heat typically diffuses at a rate of roughly 1 µm per µs in the retina, pulses longer than 1 µs are likely to induce thermal damages to the fragile photoreceptors. Currently, SRT procedures rely on Q-switch laser pulses having a duration of about 1.7 µs, mainly because shorter pulse durations are considered too dangerous due to the lack of control on the volume of the cavitation bubbles. For Q-switch pulses having a duration of 1.8 µs, a self-limitation phenomenon of the cavitation bubble size upon increase of the radiant exposure above the cavitation threshold has been reported in microcavitation experiments carried out with suspensions of porcine melanosomes in water (J. Neumann and R. Brinkmann, "*Microbubble dynamics around laser heated microparticles*", in Therapeutic Laser Applications and Laser-Tissue Interactions, R. Steiner, ed., Proc. SPIE 5142, paper 5142_82 (Oct. 17, 2003)). These experiments showed that short Q-switch pulses (e.g. 12 ns duration) produce a rapid increase of the average bubble size with radiant exposure, whereas for longer Q-switch pulses (e.g. 1.8 µs) the bubble size remains essentially constant and small over a certain range of radiant exposures (FIG. 2).

A constant bubble volume would be beneficial from a clinical perspective since bubbles of limited volume can be produced without a strong dependency over the radiant exposure, which represents a practical advantage for the clinicians in the context of variable eye transmission and pigmentation levels from patient to patient.

Overall, current techniques of microcavitation are limited for controlling both types of confinement at the same time. In applications, this translates into a limited precision for creating specific, local alterations of the medium. This lack of spatial resolution can lead to detrimental effects, as a consequence of collateral alterations created at locations that were not initially targeted. There is therefore a need for improving precision in such applications of laser-directed microcavitation.

SUMMARY

In accordance with one aspect, there is provided a method for the controlled generation of microcavitation bubbles in a medium having a liquid phase.

The method includes generating one or more laser pulses. Each laser pulse has a pulse duration and time-dependent pulse parameter controllable over the pulse duration. The method also includes irradiating the medium with the laser pulses with a radiant exposure sufficient to initiate microcavitation within the medium during each laser pulse, and controlling the time-dependent pulse parameter of each laser pulse according to a generally positive variation over the pulse duration such that the medium absorbs a greater quantity of energy from the laser pulse at an end of the pulse duration than at a beginning thereof.

In some embodiments the time-dependent pulse parameter may be the amplitude, the spectral content or the spatial profile of the laser pulses. The generally positive variation of the time-dependent pulse parameter may define various shapes, such as:
  a sawtooth-like shape having a positive slope;
  first phase of regularly increasing amplitude, followed by a second phase of sharply decreasing amplitude;
  a low initial step followed by a sharp increased amplitude phase and a sharp decrease amplitude phase, sequentially;
  a sequence of sub-pulses of gradually increasing peak amplitude.

In accordance with another aspect, there is also provided a laser system for generating microcavitation bubbles in a controlled manner in a medium having a liquid phase.

The laser system first includes a laser pulse generating assembly for generating one or more laser pulses, each laser pulse having a pulse duration and a time-dependent pulse parameter controllable over the pulse duration. The laser pulses have a radiant exposure sufficient to initiate microcavitation within the medium during each laser pulse when impinging on said medium.

The laser system further includes a pulse shaping mechanism. The pulse shaping mechanism is configured to control the time-dependent pulse parameter of each laser pulse according to a generally positive variation over the pulse duration such that the medium absorbs a greater quantity of energy from the laser pulse at an end of the pulse duration than at a beginning thereof.

In accordance with yet another aspect, there is provided a method for selectively altering an organism having a liquid phase comprising the step of generating microcavitation bubbles in said organism in a controlled manner by:
  generating a plurality of laser pulses, each laser pulse having a pulse duration and having a time-dependent pulse parameter controllable over the pulse duration;
  irradiating the organism with the laser pulses with a radiant exposure sufficient to initiate microcavitation within the organism during each laser pulse; and
  controlling the time-dependent pulse parameter of each laser pulse according to a generally positive variation over the pulse duration such that the organism absorbs a greater quantity of energy from the laser pulse at an end of the pulse duration than at a beginning thereof.

In accordance with yet another aspect, there is provided a method for selectively altering a cell having a liquid phase, comprising the step of injecting a light absorber in said cell, irradiating said light absorber with laser pulses produced by the laser system above, so as to increase permeability of said cell.

There is also provided a method for detecting a presence of a light absorber in a medium having a liquid phase. The method includes the step of irradiating said light absorber with laser pulses produced by the laser system above, thereby generating detectable microcavitation bubbles in said medium indicative of the presence of the light absorber.

Finally, there is also provided a method for processing a material using microcavitation, the material comprising a medium having a liquid phase or being in contact with a medium having a liquid phase, said method comprising the step of irradiating said medium with laser pulses produced by the laser system above.

Features and advantages of the invention will be better understood upon reading of preferred embodiments thereof with reference to the appended drawings.

BRIEF DESCRIPTION OF THE DRAWINGS

FIGS. 6A and 6B show two different dynamics observed with the same Q-switch like pulse format. FIG. 6C shows dynamics recorded when using the sawtooth-like pulse shape.

DETAILED DESCRIPTION

Figure 1:
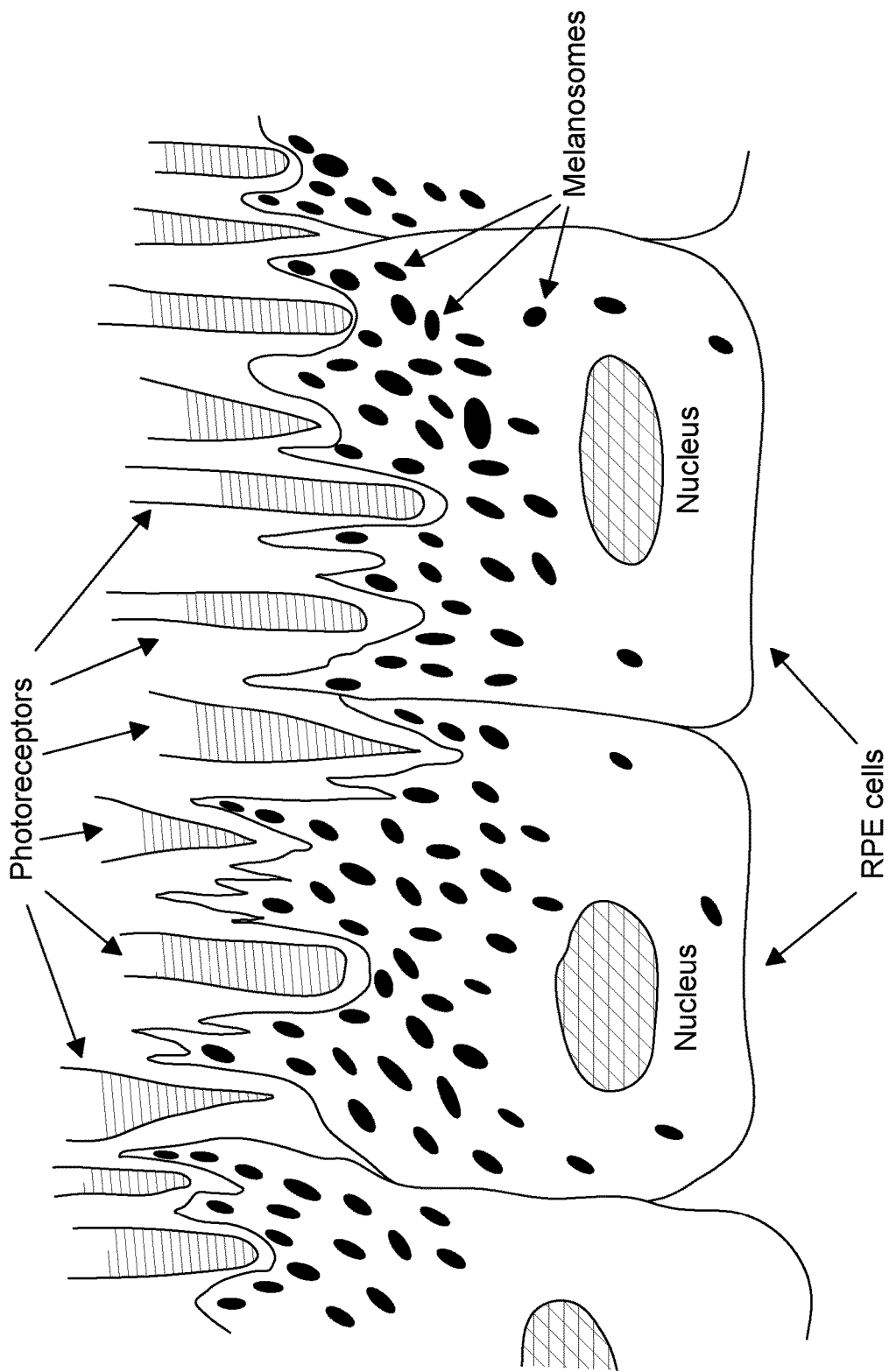
FIG. 1 (PRIOR ART) is a schematic representation of the distribution of melanosomes within RPE cells with respect to the position of photoreceptors.
Figure 2:
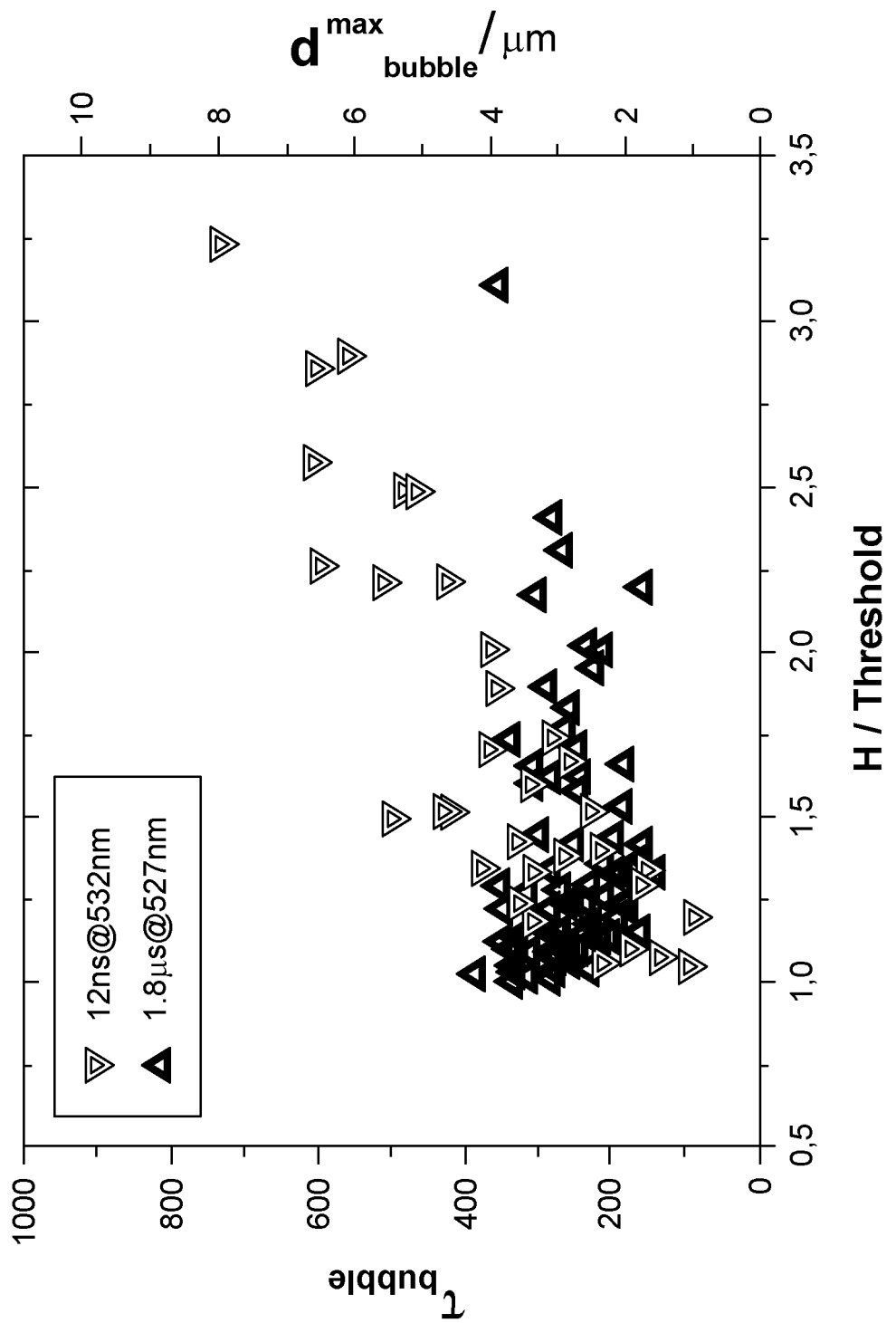
FIG. 2 (PRIOR ART) is a comparison of cavitation bubble lifetime and diameter above the threshold radiant exposure for two different Q-switch laser pulse durations, as reported by Neumann and Brinkmann.

In accordance with implementations, the tailoring of laser pulses is used to provide a better control of laser-directed microcavitation processes.

As explained above, laser-directed microcavitation involves the generation of vapor bubbles within a medium possessing a liquid phase, upon absorption of laser energy by the medium. The medium may be affected by both thermally-induced alterations resulting from heat diffusion within the medium, and by mechanically-induced alterations originating from stresses developing in the medium as the microcavitation bubbles expand and collapse. In the description below, the reference to "alterations" of a medium through microcavitation may encompass either thermally-induced alterations, mechanically-induced alterations or both. Particularly, in the case of biological media (such as, for example, living organisms or tissue), the medium can be homogeneous or heterogeneous and the "alterations" may affect the structure or the biological function of the organism, or both.

The expression "microcavitation" is typically used to refer to processes leading to the generation of transient bubbles of micrometric dimensions, but it will be generally understood that the use of language such as "microcavitation" or "microbubble" is not meant to impart any specific size limitations to the physical phenomena to which the present invention may apply.

In accordance with some implementations, there is provided a method for the controlled generation of microcavitation bubbles in a medium having a liquid phase which generally includes:

generating one or more laser pulses, each laser pulse having a pulse duration and having a time-dependent pulse parameter controllable over the pulse duration;

irradiating the medium with the laser pulses with a radiant exposure sufficient to initiate microcavitation within the medium during each laser pulse; and controlling the time-dependent pulse parameter of each laser pulse according to a generally positive variation over the pulse duration such that the medium absorbs a greater quantity of energy from the laser pulse at an end of the pulse duration than at a beginning thereof.

It will be readily understood that the elements or steps of the method as presented above are not meant to describe a consecutive series of event and that they may occur concurrently or in a different order without departing from the scope of the invention.

Examples of Applications

Controlled microcavitation may be of use for several applications, for example in the biomedical field. Particularly, when used in the field of biology or medicine, the medium having a liquid phase may be an organism, particularly a living organism, that needs to be destroyed, killed, cut, removed or altered selectively from its immediate surrounding environment (i.e. healthy tissue/organ, surrounding cells, blood or other biological fluid, cell culture medium, water, for example potable water or waste water).

More particularly, some implementations provide a method for selectively killing, destroying or altering a living organism having a liquid phase comprising the step of: generating microcavitation bubbles in said organism in a controlled manner by: generating one or more of laser pulses, each laser pulse having a pulse duration and having a time-dependent pulse parameter controllable over the pulse duration; irradiating the organism with the one or more laser pulses with a radiant exposure sufficient to initiate microcavitation within the medium during each laser pulse; and controlling the time-dependent pulse parameter of each laser pulse according to a generally positive variation over the pulse duration such that the organism absorbs a greater quantity of energy from the laser pulse at an end of the pulse duration than at a beginning thereof.

Such living organism may be a prokaryotic cell, a eukaryotic cell or a virus, particularly suspended in a biological fluid (such as blood) or in a cell culture medium. Particularly, the living organism is a tissue or an organ having a liquid phase. In a particular aspect, the organism is submitted to the method of the present invention in vivo, in vitro or ex vivo.

For example, selective alteration of cells or tissues may be necessary in ocular laser treatments, such as SRT, for selectively altering the medium surrounding the melanin pigments, thereby leading to the alteration (and eventual destruction) of the melanosomes in retinal epithelium cells.

As well, nanoparticle-assisted cellular microsurgery may be useful for tissue or organ resection, in particular for cancer treatment. Additionally, implementations of the present method and system may be carried out to produce microbubble-mediated transfection of drugs or genetic material in cells after insertion/injection of a light absorber into cells and then irradiating the absorber to increase cell permeability. The light absorber ma for example be a nanoparticle such as a gold nanoparticles, a dye, etc.

In examples of implementation described below, results were obtained for experiments illustrating the potential of tailoring of laser pulses to control microcavitation for surgical applications relying on the creation of selective alterations in tissues containing pigments that strongly absorb laser light. For such applications and the like, there may be provided a method for the treatment of a disease or a condition necessitating selectively destroying an affected tissue or organ having a liquid phase of a subject in need thereof, comprising the step of irradiating said tissue or organ with laser pulses produced by the laser system of an embodiment of the invention. More particularly, the disease or condition may be such as: kidney stones, bezoars or gallstones, cancer or an ophthalmologic condition, such as, for example: floaters (such as opacities, vitreous strands, etc.), retinal disease, glaucoma, ametropia or cataracts.

Alternatively, the present method may be carried out for laser tissue ablation or microsurgery. Particularly, surgical procedures that require precise damage confinement may use implementations of the method and/or system described herein. Examples of such procedures include amongst others: lithotripsy or surgical procedures such as tumor destruction or selective laser trabeculoplasty, retinal surgery in general such as refractive surgery or laser vitreolysis, capsulotomy or. More particularly, the method is carried out in a subject in need thereof, i.e. that is suffering from the particular medical condition. Most particularly, the subject is a mammal, preferably a human subject.

Alternatively, the method is used for selective photothermolysis, such as, for example, for tattoo or hair removal.

For such applications, one motivation is to confine the alterations within a limited, predictable volume of tissue around the absorbers, in order to spare adjacent tissues not being targeted by the treatment. For example, in selective retina therapy (SRT), the absorption of laser light by melanin pigments synthetized in the melanosomes, which are membrane-bound organelles of the retinal pigment epithelium (RPE) cells, can be exploited to selectively alter these cells by laser-directed microcavitation. As the rationale of SRT is to alter RPE cells while sparing adjacent retinal tissue layers, including the photoreceptors, it is desired to confine tissue alterations within a volume that does not include these adjacent layers. It will be readily understood, however, that the teachings of the present description are not limited to SRT applications. Medical applications including lithotripsy, cell destruction in cancer research or the treatment of other conditions such as glaucoma are other examples of possible embodiments. In some implementations, the medium may be an in vitro medium.

Additionally, the present method may be used for detecting the presence of a foreign/abnormal body that is light absorbing in a medium having a liquid phase, whereby the generation of detectable microcavitation bubbles in the medium is indicative of the presence of the foreign body. Diagnostic applications can thus be envisioned, for example for the detection of malaria (Lukianova-Hleb et al., "*Hemozoin-generated vapor nanobubbles for transdermal reagent- and needle-free detection of malaria*" PNAS 2014 111 (3) 900-905; published ahead of print Dec. 30, 2013, doi: 10.1073/pnas.1316253111). As is known in the art, malaria parasites digest hemoglobin to for intraparasite particles referred to as "hemozoin". Hemozoin strongly absorbs energy from laser pulses, which is diffused in the surrounding liquid. This leads to the generation of nanobubbles around the hemozoin. As hemozoin particles are much stronger light absorbers than hemoglobin, the presence of the bubbles is indicative of the presence of malaria parasites in the blood. The bubbles can be detected through known techniques such as optical scattering imaging or photoacoustic methods.

In other implementations, controlled microcavitation may be used in conjunction with non-biological media, inasmuch as it involves a medium has a liquid phase. Embodiments may therefore provide a method for processing a material using microcavitation, the material comprising a medium having a liquid phase or being in contact with a medium having a liquid phase. The method involves the step of irradiating the medium with laser pulses produced by a laser system according to an embodiment of the invention.

As one skilled in the art will readily understand, the reference to a medium having a liquid phase does not necessarily imply that the medium exists in liquid form prior to the bubble generation process. Indeed, in some embodiments the medium may be in solid form and heated, using the laser system dedicated to microcavitation or another heating mechanism, to fuse the medium into its liquid phase so that microbubbles may be formed therein. In other embodiments, the material being processed may not itself define the medium having a liquid phase, but may be put in contact with such a medium, for example water or the like. In such a case, microcavitation bubbles may be generated in the neighboring medium and their proximity to the material can be used to affect this material in a desired fashion.

Of course, it will be readily understood that methods and systems according to embodiments may be used in the context of other applications than those described above without departing from the scope of the present invention.

Method for the Controlled Generation of Microcavitation Bubbles

In accordance with various implementations, there is provided a method for the controlled generation of microcavitation bubbles in a medium having a liquid phase.

The method involves generating one or more laser pulses. One skilled in the art will readily understand that laser pulses may be generated by a number of devices or combination of devices, as explained further below. The plurality of laser pulses may define a pulse train emitted at a given repetition rate which can be selected in view of the various operating parameters of the method as known to those skilled in the art. The duration of each laser pulse may be defined as the time interval between the onset of the pulse and its end. Typically the pulse duration can be of the order of 1 ns to 5000 ns, as dictated by the physical factors at play in a given implementation. In accordance with one aspect, each laser pulse is characterized by a time-dependent pulse parameter which is controllable over the pulse duration, as explained below.

The method further involves irradiating the medium with laser pulses having a radiant exposure sufficient to initiate microcavitation within the medium during exposure to each laser pulse.

The expression "radiant exposure", (symbol "H"), is understood to refer to the laser energy impinging on the medium per unit area, and can for example be expressed in units of $mJ/cm^2$. As one skilled in the art will readily understand, the radiant exposure during a laser pulse is determined by both the power distribution and the spatial distribution of light within the laser pulse as a function of time. For any given implementation, a desired radiant exposure can be obtained through a proper control of the laser pulse generation conditions, as well as through the provision of one or more optical component in a path of the laser pulse which act to focus, collimate, redirect, amplify, modulate or otherwise affect the properties of the laser pulses.

Radiant exposure can be considered sufficient to initiate microcavitation within the medium during any given laser pulse if it is greater than a minimum value at which the onset of microbubble generation is observed, this minimum value being typically referred to as the "threshold radiant exposure", denoted as "$H_T$".

The method further involves controlling a time-dependent pulse parameter of each laser pulse. This control will be better understood when described with respect to exemplary embodiments in the section below, using the amplitude of the laser pulses as the time-dependent pulse parameter.

Tailoring of the Amplitude Profile of the Laser Pulses

In some implementations, the time-dependent pulse parameter is embodied by the amplitude of the laser pulses. As will be readily understood by one skilled in the art, the amplitude of light refers to the instantaneous fluxes of photons impinging on the medium, for example can be expressed in terms of instantaneous power (W) or directly in photons/s. The variation of the amplitude of a laser pulse over the duration of the pulse is often referred to in the art as the amplitude profile of the pulse or simply the "pulse shape".

In examples of implementations, both the threshold radiant exposure $H_T$ and the cavitation dynamics were found to be strongly dependent on the pulse shape. "Cavitation dynamics" is understood to refer in general to the evolution of the bubble characteristics, including its size, during its formation, growth and collapse phases. This dynamics depends on the details of the vaporization kinetics of the medium under time-dependent absorption of laser energy. Differences of up to 40% in the value of the threshold radiant exposure were noticed when using pulses of the same duration but having different pulse shapes. The pulse shape can also have a major impact on the maximum bubble volume at suprathreshold radiant exposures (above $H_T$).

In accordance with one aspect, the pulse shape or another time-dependent parameter is controlled according to a generally positive variation over the pulse duration, such that the medium absorbs more energy from the laser pulse at an end of the pulse duration than at a beginning thereof.

Figure 3:
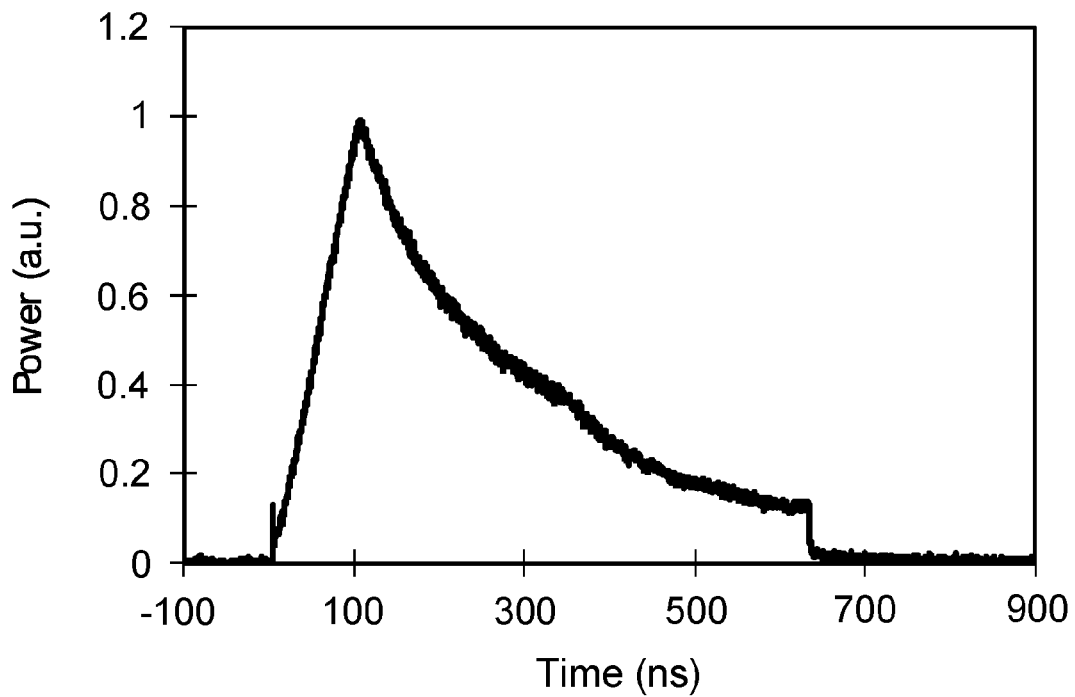
FIG. 3 (PRIOR ART) shows a Q-switch-like laser pulse shape having a total duration of 630 ns.
Figure 4:
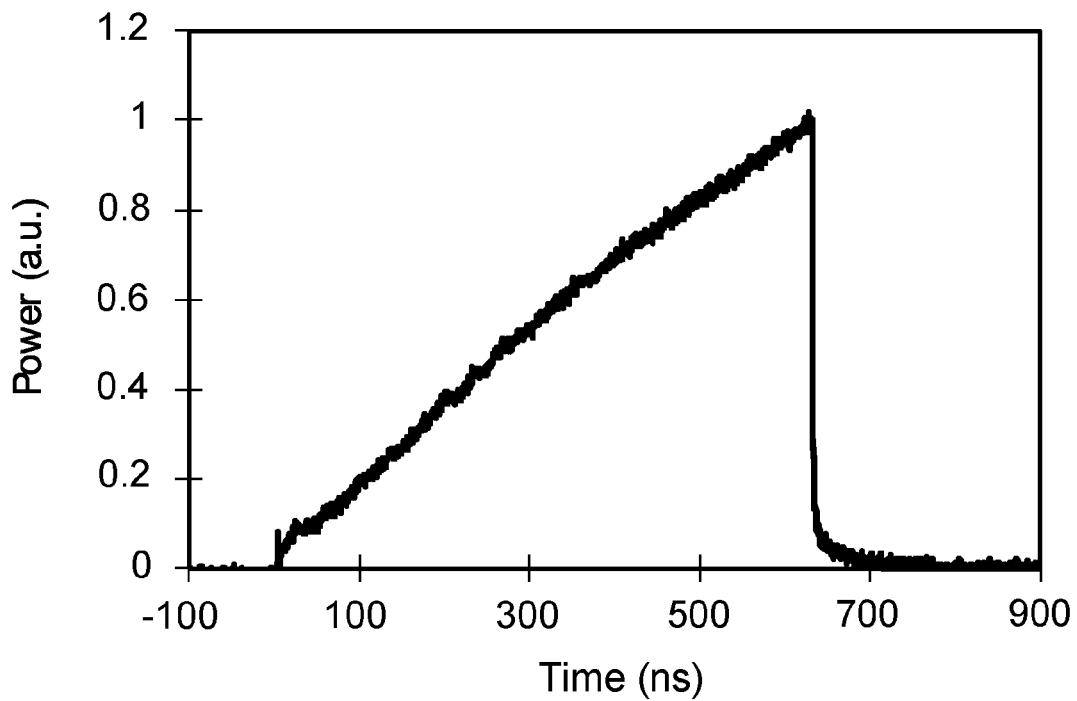
FIG. 4 shows a sawtooth-like laser pulse shape as may be used in embodiments, having a total duration of 630 ns.

Referring to FIG. 4, there is shown one example of a laser pulse having a sawtooth-like shape with a positive slope, and which defines what is generally referred to as "generally positive variation". Such a pulse shape differs strongly from the shape of pulses typically used for generating microcavitation bubbles. Typically, Q-switched lasers are used for laser-induced microcavitation, as such lasers emit pulses of the required energies using a mature and well known pulse-generating scheme. Q-switch lasers typically produce pulse shapes characterized by a steep rise time followed by a long tail, such as shown in FIG. 3 (PRIOR ART). Such a pulse shape can therefore be said to have a generally negative variation, and a medium exposed to such a pulse shape would absorb a greater quantity of energy from the laser pulse at the beginning of the pulse duration than at its end, in direct contrast with laser pulses used in embodiments described herein.

It will be readily understood that the reference to a generally positive variation should be understood to a profile which on average defines a positive slope, but that the variation need not be positive over the entire duration of the pulses. In some embodiments, the profile of the pulse amplitude or other parameter may include plateaus, peaks, valleys and or other irregular features without departing from the scope of the invention.

With additional reference to FIGS. 5 and 6A-6C, experimental results of microcavitation bubble generation using the pulse shape of FIG. 4 are shown and compared to results obtained in similar conditions but using the typical Q-switch-like shape of FIG. 3. Melanin from Sepia officinalis and bovine melanosomes suspended in water were used as models in these experiments. Using a pump-probe setup and time-resolved imaging, the threshold radiant exposure $H_T$ for the onset of microcavitation was measured upon single-pulse irradiation at a wavelength of 532 nm with different laser pulse formats having durations in the range of 2 ns to 630 ns. The cavitation dynamics and the bubble lifetime were also characterized as a function of the radiant exposure above $H_T$. A pulse-programmable, frequency-doubled pulsed fiber laser was employed to produce the different pulse formats. Details about the pulse shaping capabilities of this laser platform can be found elsewhere (P. Deladurantaye et al., *Ultra Stable, Industrial Green Tailored Pulse Fiber Laser with Diffraction-limited Beam Quality for Advanced Micromachining*, 2011 J. Phys.: Conf. Ser. 276 012017).

Figure 5:
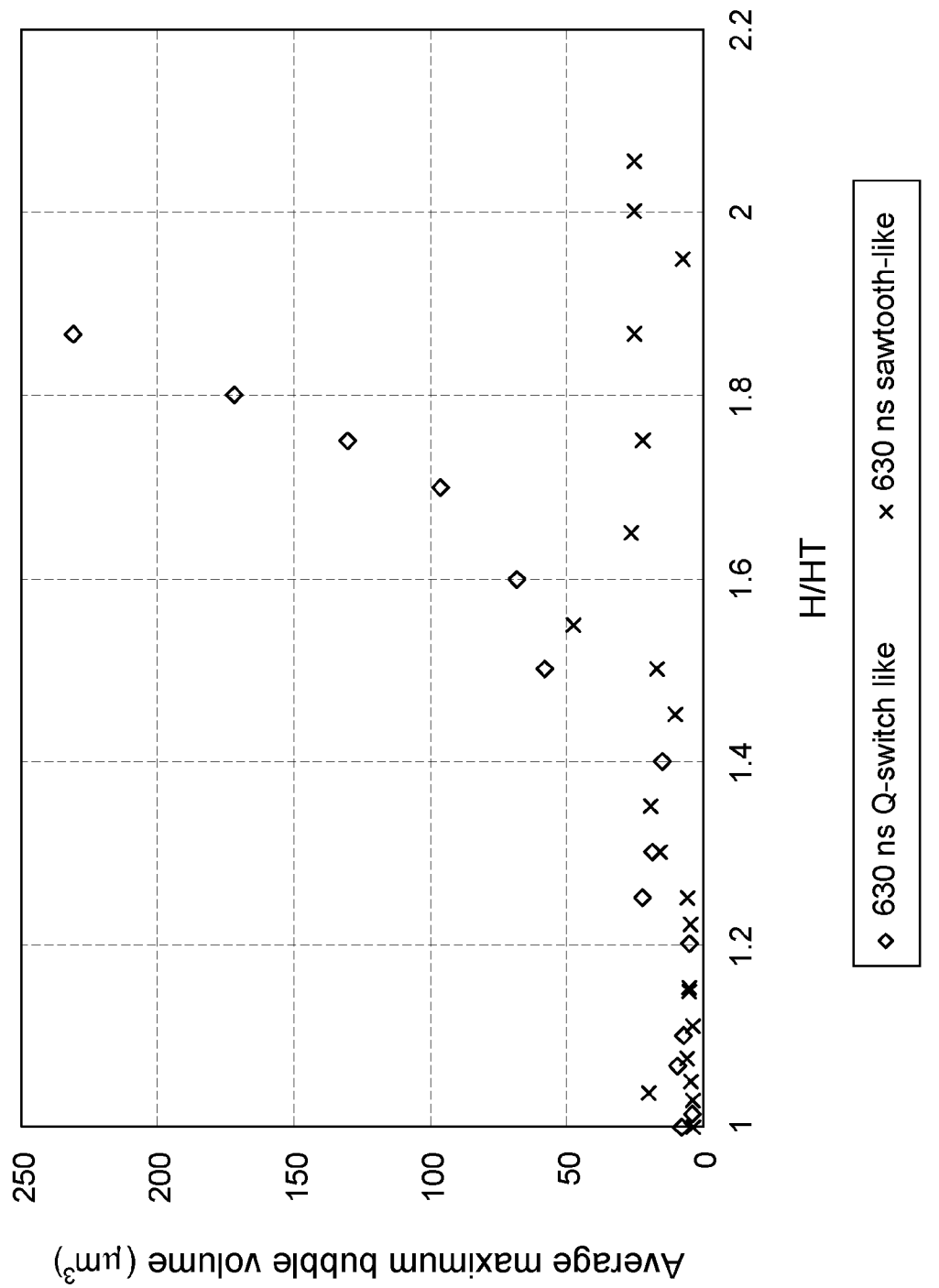
FIG. 5 is a graph plotting the average maximum cavitation bubble volume measured for the pulse shapes of FIGS. 3 and 4, respectively, as a function of radiant exposure H normalized to the threshold radiant exposure $H_T$, for suspensions of bovine melanosomes in water irradiated at 532-nm wavelength (single-pulse irradiation).

FIG. 5 compares the average maximum cavitation bubble volume measured for laser pulses having the sawtooth shape of FIG. 4 and for Q-switch-like laser pulses such as shown in FIG. 3 for different radiant exposures. All pulses in both formats had the same duration (630 ns) and the same wavelength (532 nm). The average maximum bubble volume is illustrated as a function of the radiant exposure H normalized to the threshold radiant exposure $H_T$.

In the experiment reported at FIG. 5, threshold radiant exposures of (212+21/−16) mJ/cm$^2$ and (148+16/−9) mJ/cm$^2$ were measured for the pulse shape of FIG. 3 and that of FIG. 4, respectively, and it can be observed that sawtooth-like pulses yield a threshold radiant exposure about 40% lower than Q-switch like pulses. Furthermore, the sawtooth-like shape produced bubbles having a nearly constant maximum volume over an appreciable range of radiant exposures (more than twice $H_T$), whereas for the Q-switch like shape the bubble volume increased sharply above 1.4$H_T$. Close to 2$H_T$, the Q-switch-like shape produced bubbles having an average volume about ten times larger than the volume of the bubbles generated with the sawtooth-like shape.

Figure 6:
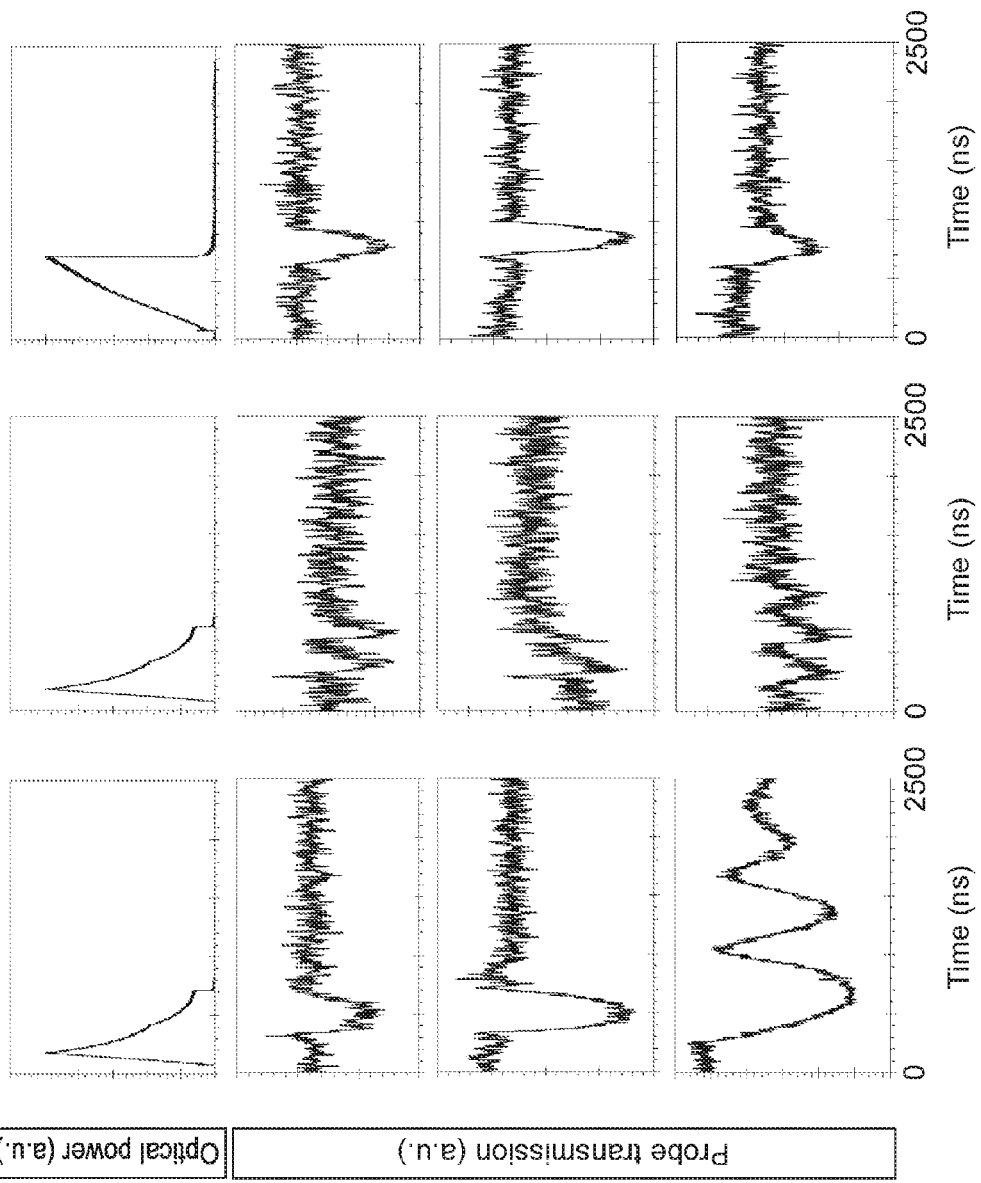
FIGS. 6A-6C show the details of the cavitation dynamics observed in the experiment described in FIG. 5. First row: pulse formats. Rows 2, 3 and 4: probe transmission for values of $H/H_T$ of 1.25, 1.50 and 1.87 respectively.

FIGS. 6A-6C presents details of the cavitation dynamics observed in the same experiment as for the results of FIG. 5. As can be observed, the Q-switch like shape produced two types of responses: one characterized by bubbles whose lifetime scaled with radiant exposure (FIG. 6A) and the other by multiple short-lived bubbles with lifetimes nearly independent of radiant exposure (FIG. 6B). The behavior depicted in FIG. 6A was observed for the vast majority (about 80%) of measurements carried out with the Q-switch like shape for radiant exposures between 1.5$H_T$ and 1.87$H_T$. Consequently, the potential of bubble size control through self-limitation as described by Neumann and Brinkmann (cite above) appears limited for a Q-switch-like pulse format such as the one shown in FIG. 3.

With the sawtooth-like shape of FIG. 4, only relatively short-lived bubbles with lifetimes nearly independent of radiant exposure where observed (FIG. 6C). It is of interest to mention that the threshold radiant exposure obtained with the sawtooth-like shape (148 mJ/cm$^2$) is 4.2 times lower than the threshold reported by Neumann and Brinkmann (620 mJ/cm$^2$) for a pulse duration of 1.8 µs, with still no increase of the bubble volume above $H_T$ despite the shorter pulse duration.

Taken together, the results reported in FIGS. 5 and 6A-6C demonstrate that pulse tailoring, here embodied by a sawtooth-like shape, allows for optimizing both thermal and photomechanical confinements.

The lower threshold radiant exposure obtained using laser pulses having the sawtooth-like shape instead of the Q-switch-like shape can be at least partially understood using relatively simple physical arguments. At threshold, microcavitation is initiated near the end of the laser pulse, as the threshold corresponds to the condition for which all of the pulse energy is required to cause vaporization of the medium. Since for the Q-switch-like shape more energy is provided at the beginning of the pulse, more energy is required to reach the critical nucleation temperature because heat diffusion is more important during the rest of the pulse than for the sawtooth-like shape. The quick energy coupling arising with the Q-switch-like shape produces a steeper thermal gradient early in the pulse. Due to this steeper temperature gradient, heat losses are more important during the last part of the Q-switch-like pulse, compared to the sawtooth-like shape. Because of these higher thermal losses, more laser energy is required to reach the nucleation temperature when using the Q-switch-like pulse.

As regards to the cavitation dynamics above threshold, the situation is more complex and more aspects need to be considered to understand the observed differences. Important aspects include the formation of a thermally insulating vapor blanket around the absorption centers and the volume of superheated, metastable media (J. Neumann and R. Brinkmann, *Self-limited growth of laser-induced vapor bubbles around single microabsorbers*, Applied Physics Letters; Vol. 93, Issue 3, Jul. 21, 2008). The latter determines the amount of energy stored in the medium that can be converted into kinetic energy of the bubble during its expansion. An interpretation based on qualitative arguments is proposed for the results discussed above. The increase of the radiant exposure above the threshold with pulses of Q-switch like format gives rise to steeper and steeper temperature gradients at the beginning of the pulse, which, in turn, results in increasingly important heat fluxes that can be converted into bubble energy. Indeed, because more heat losses occur when delivering more energy at the beginning of the pulse than at the end, the thermal boundary layer thickness is larger with Q-switch-like pulse formats compared to sawtooth-like formats. Consequently, more energy is available from the medium to drive bubble expansion when Q-switch-like pulse formats are employed, and larger bubbles are produced. One aspect of pulse tailoring-based control of microcavitation is therefore linked with the choice of shapes that minimize heat losses, since heat losses directly determine the volume of medium that is thermally affected, while also driving bubble growth.

Furthermore, with the sawtooth-like shape, it can be suggested that cavitation bubbles are shielding laser energy absorption for the most intense part of the pulse, whereas for the Q-switch like shape this most intense part is not shielded for a broad range of radiant exposures above threshold. The shielding effect provided by bubble growth prevents useless absorption of energy from the part of the pulse that follows bubble incipience. With the Q-switch like format, the medium is irradiated upfront with the most powerful part of the pulse, yielding larger bubbles for the reasons exposed above. On the other hand, for the sawtooth-like format the shielding effect "shuts down" intense, useless parts of the pulse that could otherwise produce larger temperature gradients and drive growth of larger bubbles.

Another possible origin of the more explosive bubble behaviors observed with the Q-switch-like may be linked with the evolution of the bubble incipience time $\tau_{inc}$ at suprathreshold radiant exposures. As the radiant exposure is increased above threshold, the higher heating rates allow the nucleation temperature to be reached earlier, in other words $\tau_{inc}$ decreases with increasing radiant exposure. As such, $\tau_{inc}$ can be seen as an effective initial heating time or effective pulse duration for a given radiant exposure, since the expanding bubble can thermally insulate the melanosome and to some extent shield further absorption of laser energy at later times. The inventors have experimentally and theoretically shown that $\tau_{inc}$ is shorter for the Q-switch format than for the sawtooth format, at a given radiant exposure. As pointed out by Neumann and Brinkmann, shorter durations lead to more explosive vaporizations. Therefore, the larger bubble volumes produced by Q-switch-like formats would be associated with a shorter effective heating time or pulse duration at a given suprathreshold radiant exposure.

From the discussion above, it will be readily understood that the benefits of pulse tailoring for the control of microcavitation are not limited to sawtooth-like pulse shapes. In alternative embodiments, similar advantages may be obtained from a variety of laser pulse amplitude profiles. As will be readily understood by one skilled in the art, this may for example be achieved by choosing a profile that promotes a higher average energy absorption by the medium during a second phase of the pulse than during a preceding first phase, as is the case with the sawtooth shape with a positive slope. Indeed a variety of pulse shapes having a generally positive variation over the pulse duration can provide the shielding effect described above, if it is such that the medium absorbs a greater quantity of energy from the laser pulse at an end of the pulse duration than at the beginning thereof. The pulse shape may for example be said to define a crescendo, or having a greater amplitude at a later moment in time than it does at the onset of the pulse.

Figure 7:
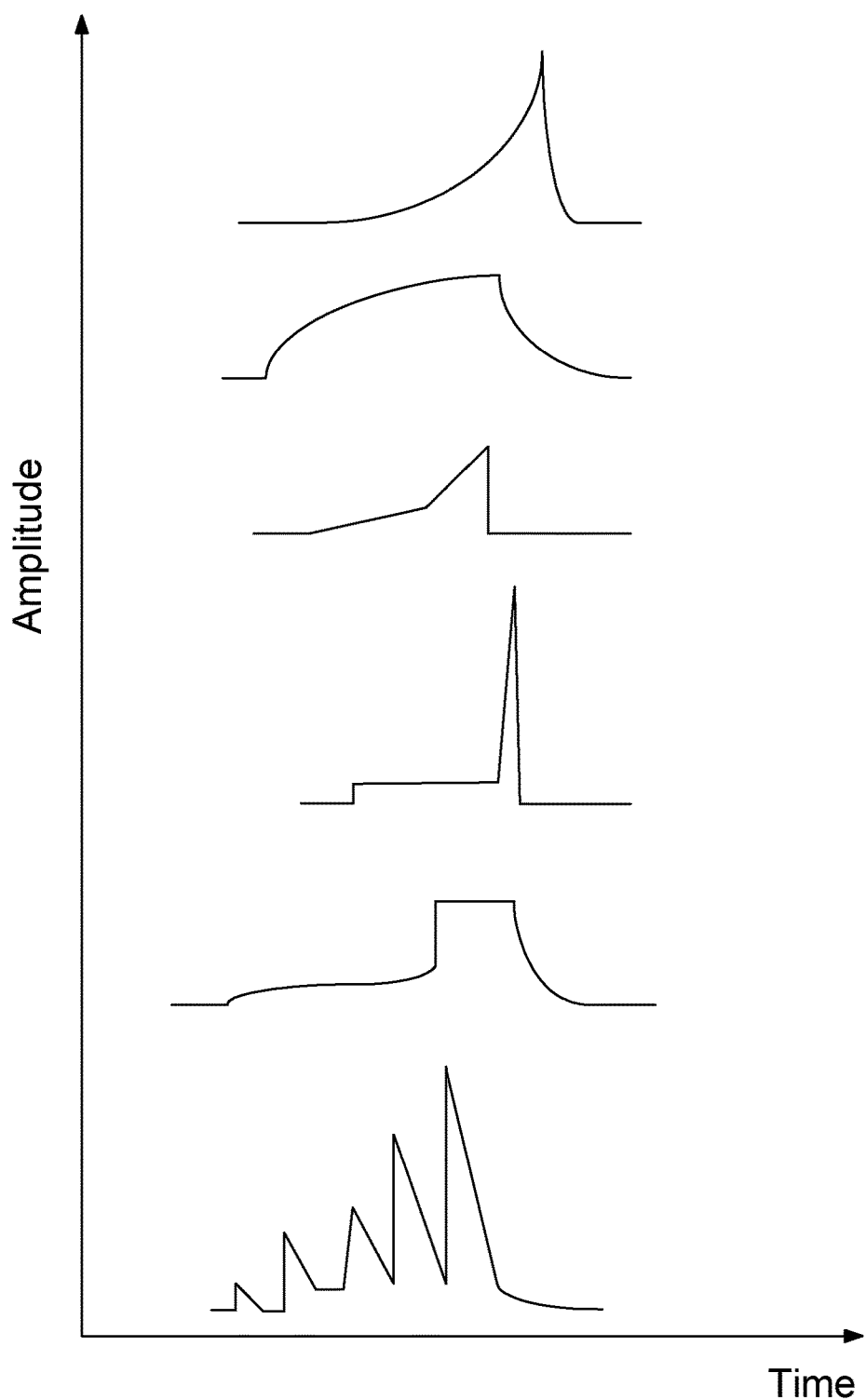
FIG. 7 illustrates six (6) examples of pulse shapes that may be used in embodiments of the invention.

Other, non-limitative examples of laser pulse shapes that may be of interest are shown in FIG. 7. From top to bottom, the first three pulse shapes are shown to include a first phase of regularly increasing amplitude, followed by a second phase of sharply decreasing amplitude. In the next two examples, the illustrated pulse shapes include an initial phase defining a low step, followed by a sharp increasing amplitude phase and a sharply-decreasing amplitude phase, sequentially, with an optional plateau therebetween. Finally, in the bottommost illustrated example the pulse shape is shown to include a sequence of triangular sub-pulses of gradually increasing peak amplitude.

Figure 8:
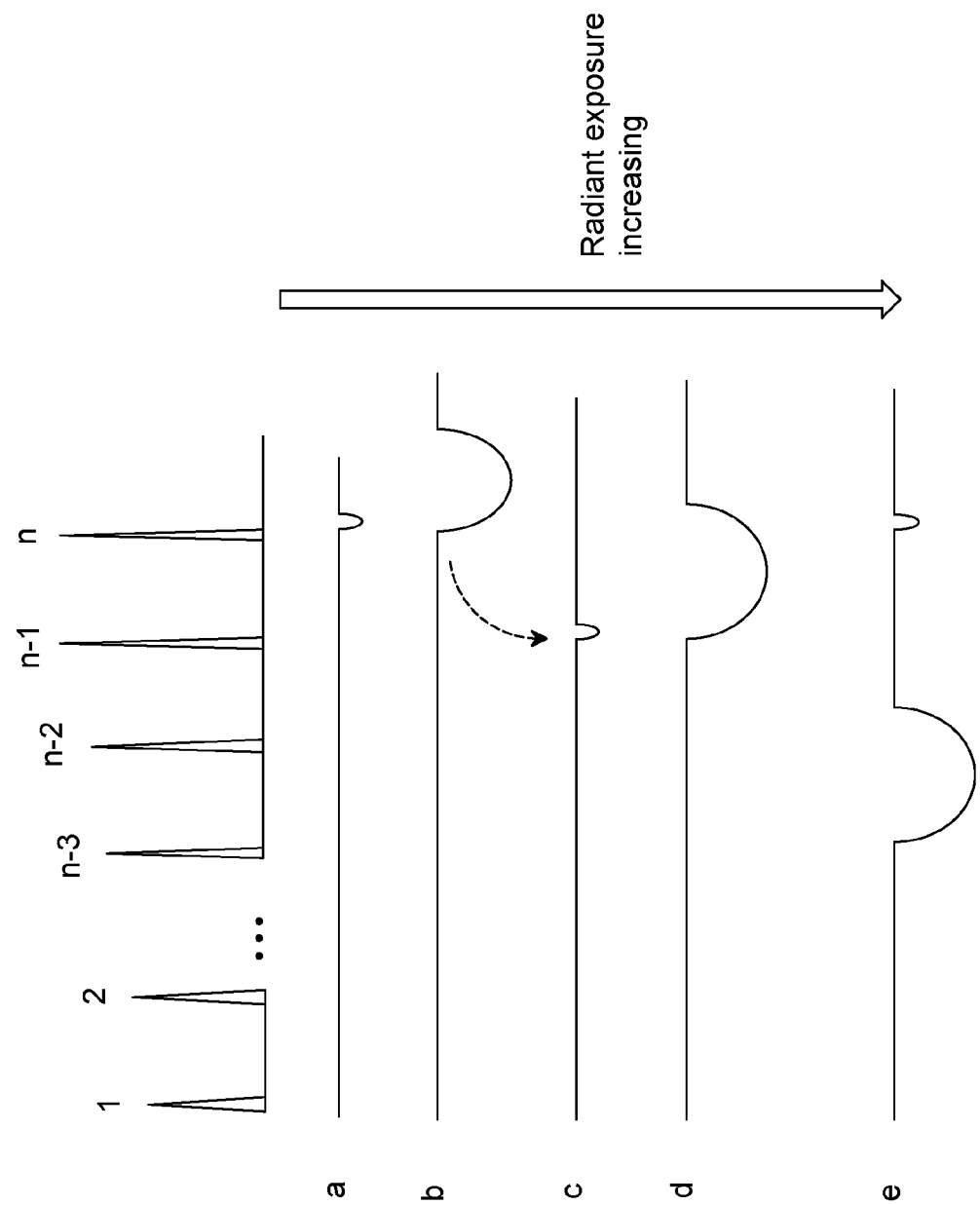
FIG. 8 illustrates the control of cavitation dynamics achievable with a pulse format including multiple sub-pulses.

Referring to FIG. 8, there is shown another embodiment where the laser pulse shape is defined by a sequence of n sub-pulses of gradually increasing peak amplitude. In such an implementation, in addition to the time-dependent pulse parameter such as the pulse shape or spectrum, the time delays separating individual sub-pulses within the pulse can be used to control the microcavitation bubble generation process. As illustrated, at threshold, that is, if the set of n sub-pulses collectively provides a radiant exposure equal to or exceeding the threshold radiant exposure, cavitation starts on sub-pulse n (line a). Upon increasing the energy of the laser pulses, and therefore increasing the radiant exposure, the maximum size of this bubble increases as shown in line b. Cavitation however still starts during exposure to the $n^{th}$ sub-pulse. If the radiant exposure is increased further, at some point enough energy is available from the preceding (n−1) sub-pulse to initiate microcavitation, leading to a "hopping" effect (line c). This jump causes a reset of the maximum bubble size. This hopping process repeats itself as the radiant exposure is further increased (lines d-e), with the cavitation now starting on pulse n−2, then n−3 and so on. At higher radiant exposures, multiple bubbles can be generated and the hopping effect can combine with shielding effects. Indeed, because bubbles can scatter and/or diffract light, they can shield absorption centers from laser light during their lifetime. In this example, this happens for radiant exposures such that the lifetime of the bubble initiated at a given sub-pulse is of the same order or larger than the delay between this sub-pulse and the subsequent one. The lifetime of the created bubbles can therefore be controlled so that it will not exceed a maximum value through a proper determination of the sub-pulse characteristics and the time delay between them.

Tailoring of Other Time-Dependent Parameters

In the examples given above, the amplitude profile of the light pulses was tailored as a function of time to obtain the desired pulse shape. Other time-dependent pulse parameters may however be tailored to achieve similar results. For example, in other embodiments, the time-dependent pulse parameter may be embodied by the spectral content of the laser pulse. As the absorption of a medium generally varies with the laser wavelength, spectral tailoring of the laser pulses can indeed be exploited to tune the rate of energy absorption with the purpose of controlling microcavitation. Such implementations may therefore include tailoring the spectral profile of the laser pulses as a function of time according to a generally positive variation, that is, using wavelengths at the end of the pulse duration which are more strongly absorbed by the medium than wavelengths at the beginning of the laser pulses. In other embodiments, the time-dependent pulse parameter may be embodied by the spatial profile of the laser pulse. For example, changes of the beam shape during the pulse duration can be employed to dynamically adjust the irradiance incident within a given volume of medium with the purpose of controlling microcavitation through precise tuning of the rate of laser energy absorption in that volume.

Laser Systems

In accordance with another aspect, there is also provided a laser system for generating microcavitation bubbles in a medium having a liquid phase in a controlled manner.

Figure 9:
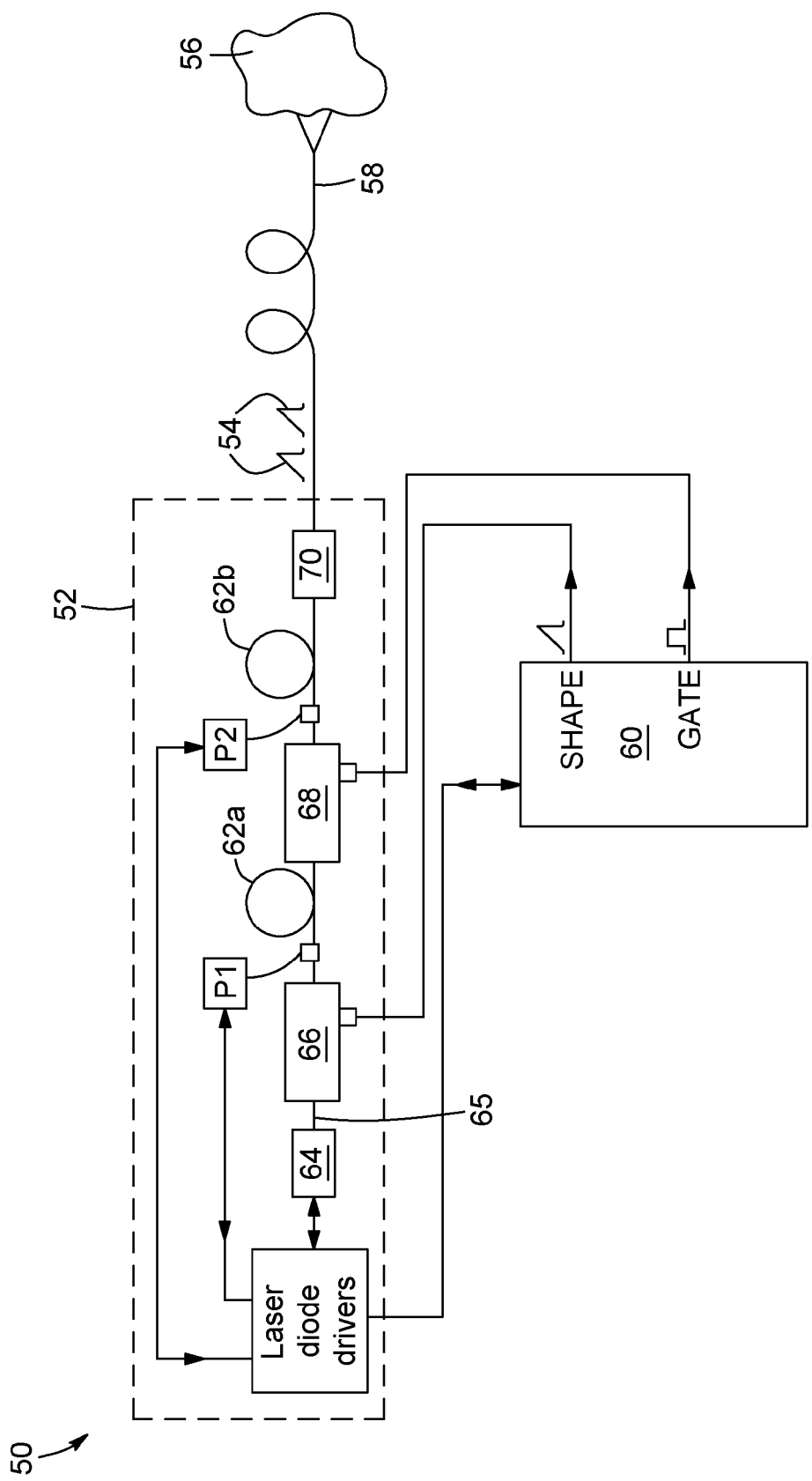
FIG. 9 schematically illustrates a laser system for generating microcavitation bubbles according to one embodiment.

Referring to FIG. 9, there is shown one example of a laser system 50 according to one embodiment.

The laser system 50 includes a laser pulse generating assembly 52 for generating a plurality of laser pulses 54. As explained above, each laser pulse has a duration and a time-dependent pulse parameter controllable over the pulse duration. In the illustrated embodiment, control of the amplitude of the laser pulses is provided, and the time-dependent pulse parameter may therefore be embodied by the amplitude profile or pulse shape of the laser pulses 54.

The laser pulses 54 have a radiant exposure sufficient to initiate microcavitation within the medium 56 during each laser pulse 54 when impinging on this medium. The radiant exposure may be controlled through an adjustment of the optical power and spatial distribution of the laser pulses, for example through a control of their generation parameters and/or through additional optical components.

In one example, the laser pulses 54 outputted by the laser pulse generating assembly 52 may be carried by an optical fiber 58 toward the medium 56. It will be readily understood that any number of optical components guiding, redirecting, focussing or otherwise affecting the laser pulses may be provided between the output of the laser pulse generating assembly 52 and the medium 56. Furthermore, the laser system 50 may be integrated in a larger apparatus or installation including any number of additional components including electronic, digital, communications, mechanical, optical components and the like without departing from the scope of the invention.

In the illustrated example, the laser pulse generating assembly 52 is based on a Master Oscillator, Power Amplifier (MOPA) architecture. The laser pulse generating assembly 52 therefore includes a seed light source 64, acting as a master oscillator, and at least one optical power amplifier, first and second amplifiers 62a, 62b being shown in the example of FIG. 9. Still in this example, the seed light source 64 operates preferably in a continuous wave (CW) regime to generate a continuous light beam 65. The seed light source 64 may for example be a laser diode, but any other light source generating an appropriate CW beam could be considered, such as for example a filtered ASE (Amplified spontaneous emission) source, a superfluorescent source, a CW fiber laser or a fiber coupled CW bulk solid-state laser source. The continuous light beam 65 preferably has a spectral shape which will determine the spectral shape of the laser pulses 54 outputted by the laser pulse generating assembly 52. Advantageously, the seed light source may be selected or replaced depending on the required spectral profile of the outputted light. Alternatively, a wavelength-tunable laser diode may be used. Additional components may optionally be provided downstream the laser diode to modify its spectral shape. An optical isolator may also be provided downstream the seed laser diode to prevent feedback noise from reaching it.

The first and second amplifiers 62a and 62b are provided in series in the path of the light beam generated by the seed light source. An appropriate optical pump signal from optical pump source P1, propagating either backward or forward through the gain medium of the first amplifier 62a, maintains the required population inversion therein. Similarly, the second amplifier 62b may be forward or backward pumped by a suitable optical pump source P2. Both the first and the second amplifiers 62a and 62b may for example be embodied by a length of polarization-maintaining aluminosilicate optical fiber doped with rare earth elements such as Erbium, Ytterbium, Holmium, Praseodymium, Neodymium or Thulium. In yet other embodiments, additional optical components are employed for optimizing the pulsed laser source stability, such as optical isolators, polarizers, filters, etc. In a specific embodiment, the first and second amplifiers 62a and 62b may include a Semiconductor Optical Amplifier (SOA). Although FIG. 9 shows two amplifications stages in the laser pulse generating assembly, different numbers of amplifiers may be used in other implementations. In some embodiments, an amplifier chain comprising several cascaded amplifier stages is used for the final pulse amplification. In a particular embodiment, the amplifier chain may include at least one DPSS (diode-pumped solid state) amplifier stage based on gain medium like Nd:YAG or Nd:YVO$_4$. Those skilled in the art will recognize numerous variations and alternatives.

Still referring to FIG. 9, in the illustrated embodiment the laser pulse generating assembly 52 further includes a first optical amplitude modulator 66 temporally modulating the continuous light beam 65, and thereby converting it into laser pulses 54. The first amplitude modulator 66 may for example be embodied by a Lithium Niobate Mach-Zehnder electro-optic modulator suitable for generating optical pulses with controlled features at the nanosecond scale. In other embodiments, other modulation schemes, such as based on an acousto-optic modulator, an electroabsorption modulator, etc. could also be considered. The optical input port of the first modulator 66 is coupled to the seed light source 64 to receive the continuous light beam 65 therefrom. Preferably, the whole laser pulse generating assembly 52 is an all-fiber device, but it will be understood by one skilled in the art that additional optical components such as mirrors, lenses, spectral shaping elements or any other appropriate element may be provided between the CW light source 64 and the first modulator 66 without departing from the scope of the present invention.

The laser pulse generating assembly 52 may also include a second optical amplitude modulator 68, interposed between the two amplifiers 62a and 62b. According to some embodiments, the final shape of the laser pulses 54 outputted by the laser pulse generating assembly 54 will be determined by the combined action of both modulators 66 and 68.

The laser system 50 further includes a pulse-shaping mechanism. The pulse shaping mechanism is configured to control the time-dependent pulse parameter of each laser pulse 54 according to a generally positive variation over the pulse duration, such that the medium 56 absorbs a greater quantity of energy from the laser pulse 54 at an end of the pulse duration than at its beginning. As explained above, the time-dependent pulse parameter may be the amplitude, the spectral content or the spatial shape of the laser pulses. Suitable shapes having a generally positive variation can be for example a sawtooth shape, another one of the shapes illustrated in FIG. 7 or other similar shapes allowing the optimizing of thermal and photomechanical confinements, as also explained above.

It will be readily understood that the pulse shaping mechanism may be embodied by any device or combination of devices apt to control the laser pulse generating assembly in order to produce the desired pulse shape. In the illustrated embodiment of FIG. 9, the pulse shaping mechanism is embodied by a digital pulse shaping module 60. The digital pulse shaping module 60 provides control signals to components of the laser pulse generating assembly 52 in order to control the pulse shape of the laser pulses 54. In the illustrated embodiment, the control signal are embodied by a SHAPE signal and a GATE signal respectively controlling the opening and closing of the first and second amplitude modulators 66 and 68. The first and second modulators 66 and 68 may be partially or fully synchronized with each other, depending on the shape desired for the resulting laser pulses. The term "synchronized" is used herein as describing the joint timing of the opening and closing of the first and second modulators 66 and 68, taking into account the transit time of the light between both modulators. For example, the two modulators 66 and 68 will be considered fully synchronized if the second modulator 68 opens exactly at the instant the leading edge of the pulse generated by the first modulator 66 reaches it, and closes at the instant this pulse ends. Synchronization of the two modulators 66 and 68 may be used advantageously to control the pulse shape of the laser pulses. For example, by setting the two modulators 66 and 68 partially out of synchronization, pulses of a very small width may be obtained. Combining drive pulses of different durations and shapes may also advantageously be used to tailor the resulting light pulses to a wide range of specifications and with a very high time resolution.

The digital pulse shaping module 60 may be embodied by various configurations apt to provide control signals of the desired shape and resolution. One such platform is for example described in U.S. Pat. No. 8,073,027 (DELADURANTAYE et al.), the contents of which being incorporated herein by reference. It is however understood that in other embodiments pulse shaping control may be performed using different components which may be digital or analog without departing from the scope of the invention.

In some implementations, when it is desired to work with laser pulses at a wavelength which is a harmonic of the fundamental laser wavelength, the laser pulse generating assembly may further include one or more frequency conversion modules 70, for example following the second optical amplifier or optical amplifier chain. As the frequency conversion is non-linear, the pulse shaping capacity of the digital pulse shaping module may compensate the nonlinearity so as to generate precisely the desired optical pulse shape at the harmonics wavelengths.

Figure 10:
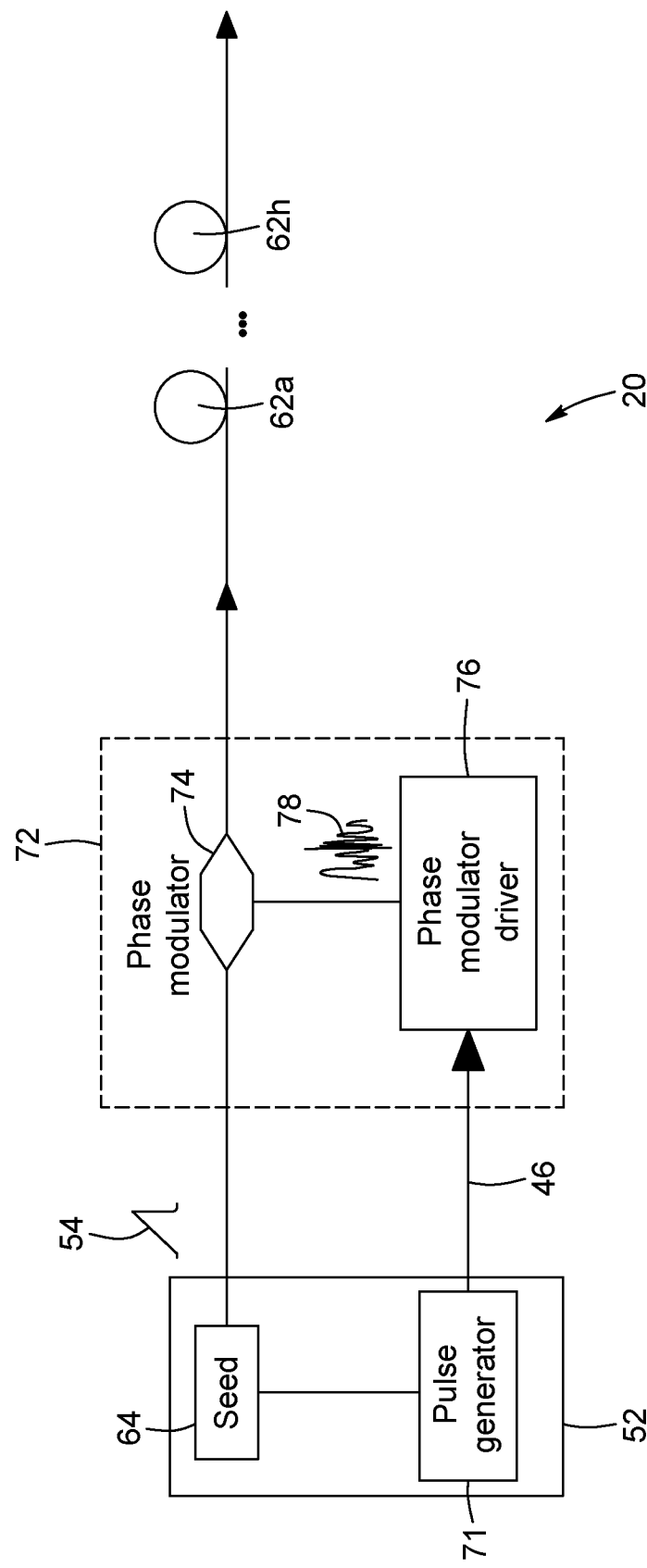
FIG. 10 schematically illustrates a laser system for generating microcavitation bubbles according to another embodiment.

Referring to FIG. 10, there is shown another example of a laser system 50 for generating microcavitation bubbles, according to one implementation.

The illustrated laser system 50 of FIG. 10 again has a Master Oscillator Power Amplifier (MOPA) architecture. In this embodiment, the laser pulse generating assembly 52 includes a seed light source 64 generating the laser pulses 54. A series of optical fiber amplifiers 62a, . . . 62n are provided downstream the laser pulse generating assembly 52 to provide light amplification.

The seed light source 64 may be embodied by a semiconductor laser diode of any appropriate configuration such as a Fabry-Perot cavity, a distributed-feedback diode, an external-cavity diode laser (ECDL), etc. A pulse generator 71 electrically drives the seed light source 64 to control the pulse characteristics. In some embodiments, the pulse generator 71 may define the pulse shaping mechanism configured to control the time-dependent pulse parameter of the laser pulses according to a generally positive variation over the pulse duration, as explained above. In some variants, the pulse shaping mechanism may further include a spectrum tailoring module 72, as for example illustrated in FIG. 10. The spectrum tailoring module can tailor the spectral profile of the laser pulses 54 generated by the laser pulse generating assembly 52. In the illustrated embodiment, the spectrum tailoring module 72 includes a phase modulator 74 which imposes a time-dependent phase variation on each laser pulse 54 therethrough. Preferably, a phase modulator driver 76 drives the activation of the phase modulator 74 through a phase variation drive signal 78 providing the desired phase variation. The phase modulator 74 may be embodied by an electro-optic component based modulator such as well-known in the art. The electro-optical material included in the phase modulator can be $LiNbO_3$, $LiTaO_3$, $KNbO_3$ or any other appropriate nonlinear material. Alternatively, the phase modulator may be based on an acousto-optical component such as an acousto-optic modulator.

Advantageously, the spectral tailoring module may be used to control the spectral content of the laser pulses according to the principles explained above. Furthermore, spectral tailoring may alternatively or additionally provide mitigation of non-linear effects for high power pulses. More details on spectral tailoring may for example be described in U.S. Pat. No. 7,974,319 (DELADURANTAYE et al.), the contents of which is incorporated herein by reference.

It will be readily understood that the embodiments shown in FIGS. 9 and 10 are just some of a number of possible implementations of a laser system according to an aspect of the invention. For example, in some variants the seed light source may be a pulses laser source, directly modulated by control signals from the pulse shaping mechanism to generate the laser pulses. Pulsed seed laser sources may be combined with external optical modulators for additional pulse shaping. In other implementations, the pulse shaping mechanism may provide a control the spatial profile as the time-dependent parameter of the laser pulses. Spatial tailoring may be accomplished by systems such as described in U.S. Pat. No. 8,254,015 (TAILLON et al.), the contents of which being incorporated herein by reference. Other laser systems suitable for use in the context of the present method include, for example, model PPL 400 laser from PicoQuant, Spectra-Physics' Quasar laser and laser model PyroFlex 25 from Electro-Scientific Industries.

Of course, numerous modifications could be made to the embodiment above without departing from the scope of the present invention.

The invention claimed is:

1. A method for the generation, in a medium having a liquid phase, of microcavitation bubbles of maximum volume controlled over at least twice a threshold radiant exposure, comprising:
    using a laser system comprising a pulse shaping mechanism, generating one or more laser pulses, each laser pulse having a pulse duration between 1 ns and 5000 ns and an energy selected to deliver a radiant exposure sufficient to initiate microcavitation within the medium during the pulse duration of each laser pulse, the pulse shaping mechanism imposing on each laser pulse a tailored amplitude profile over said pulse duration selected to deliver a greater quantity of energy to the medium during an end portion of the pulse duration than during a beginning portion thereof; and
    irradiating the medium with the laser pulses.

2. The method according to claim 1, wherein the pulse shaping mechanism comprises a digital pulse shaping module.

3. The method according to claim 2, wherein the laser system comprises a seed light source and first and second amplitude modulators, the digital pulse shaping module providing control signals to the first and second amplitude modulators.

4. The method according to claim 1, wherein the pulse shaping mechanism comprises a pulse generator electrically driving a seed light source.

5. The method according to claim 1, wherein the tailored amplitude profile of each light pulse defines a sawtooth-like shape having a positive slope.

6. The method according to claim 1, wherein the tailored amplitude profile of each light pulse defines a first phase of regularly increasing amplitude followed by a second phase of decreasing amplitude, the second phase being shorter than the first phase.

7. The method according to claim 1, wherein the tailored amplitude profile of each light pulse defines an initial step followed by an increasing amplitude phase and a decreasing amplitude phase, sequentially.

8. The method according to claim 1, wherein the tailored amplitude profile of each light pulse defines a sequence of sub-pulses of gradually increasing peak amplitude.

9. The method according to claim 1, wherein the tailored amplitude profile of each light pulse has a negative skew.

* * * * *